(12) United States Patent
Bianchi et al.

(10) Patent No.: US 12,336,710 B2
(45) Date of Patent: Jun. 24, 2025

(54) EXTRACTION DEVICE FOR BONE STAPLES

(71) Applicant: MEDACTA INTERNATIONAL SA, Castel San Pietro (CH)

(72) Inventors: Riccardo Bianchi, Castel San Pietro (CH); Sascha Berberich, Castel San Pietro (CH); Francesco Siccardi, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 526 days.

(21) Appl. No.: 17/774,291

(22) PCT Filed: Nov. 4, 2020

(86) PCT No.: PCT/IB2020/060339
§ 371 (c)(1),
(2) Date: May 4, 2022

(87) PCT Pub. No.: WO2021/090185
PCT Pub. Date: May 14, 2021

(65) Prior Publication Data
US 2022/0387029 A1     Dec. 8, 2022

(30) Foreign Application Priority Data
Nov. 5, 2019   (IT) .......................... 102019000020392

(51) Int. Cl.
*A61B 17/076* (2006.01)
*A61B 17/064* (2006.01)
*A61B 17/29* (2006.01)

(52) U.S. Cl.
CPC ........ *A61B 17/076* (2013.01); *A61B 17/0642* (2013.01); *A61B 2017/2923* (2013.01)

(58) Field of Classification Search
CPC ............ A61F 2/0811; A61F 2002/0817; A61F 2002/0823; A61F 2002/0829;
(Continued)

(56) References Cited

U.S. PATENT DOCUMENTS 4,569,469 A * 2/1986 Mongeon ............... A61B 17/88
                                                          206/338
5,163,519 A * 11/1992 Mead ...................... B25D 9/14
                                                           173/91
(Continued)

FOREIGN PATENT DOCUMENTS

| EP | 2755567 A1 | 7/2014 |
| EP | 3441016 A1 | 2/2019 |

OTHER PUBLICATIONS

International Search Report and Written Opinion issued in PCT/IB2020/060339, mailed Feb. 15, 2021, 16 pages.

*Primary Examiner* — Shaun L David
*Assistant Examiner* — Rachael L Geiger
(74) *Attorney, Agent, or Firm* — Meunier Carlin & Curfman LLC (57) ABSTRACT

An extraction system for bone staples provided with a first and a second element, comprising a main gripping body having a distal end and a proximal end. The device comprises, in addition, a central rod provided with a proximal end and a distal end, the latter adapted to couple with the first element of the staple. The central rod slides axially within the main gripping body between a first position and a second position by means of suitable movement means. The device has a plurality of abutment elements protruding in the axial
(Continued)

direction from the distal end of the main body, which are arranged circumferentially around the central rod, adapted to act on the second element of the staple to obtain, in cooperation with the movement of the central rod, the separation of the second element of the staple from the first element of the staple and the removal thereof.

12 Claims, 9 Drawing Sheets

(58) Field of Classification Search
CPC ...... A61F 2002/0835; A61F 2002/0841; A61F 2002/0847; A61F 2002/0852; A61F 2002/0858; A61F 2002/0864; A61F 2002/087; A61F 2002/0876; A61F 2002/0882; A61B 17/064; A61B 17/128; A61B 17/1285; A61B 17/076
See application file for complete search history.

(56) References Cited

U.S. PATENT DOCUMENTS

| | | | | |
|---|---|---|---|---|
| 5,352,229 | A * | 10/1994 | Goble | A61B 17/0642 606/220 |
| 5,879,371 | A * | 3/1999 | Gardiner | A61B 17/0469 606/147 |
| 6,709,439 | B2 * | 3/2004 | Rogers | A61B 17/92 606/86 R |
| 2009/0264900 | A1 * | 10/2009 | Paz | A61B 17/076 606/151 |
| 2010/0280555 | A1 * | 11/2010 | Aflatoon | A61F 2/4405 606/279 |
| 2014/0277516 | A1 * | 9/2014 | Miller | A61B 17/0642 623/18.11 |
| 2016/0174980 | A1 | 6/2016 | Heftman | |
| 2016/0242771 | A1 * | 8/2016 | Weinstein | A61B 17/842 |
| 2016/0346023 | A1 * | 12/2016 | Bouduban | A61B 17/0644 |
| 2017/0215879 | A1 * | 8/2017 | Weinstein | A61B 17/0401 |
| 2018/0008819 | A1 | 1/2018 | Halpern et al. | |
| 2024/0315696 | A1 * | 9/2024 | Hannah | A61B 17/0682 |

* cited by examiner

EXTRACTION DEVICE FOR BONE STAPLES

The present application is a national stage of International Application No. PCT/IB2020/060339, filed on Nov. 4, 2020, which claims the priority from Italian Patent Application No. 102019000020392, filed on Nov. 5, 2019, both of which are hereby incorporated by reference in their entireties.

This invention relates to a bone staple extraction system. In particular, the invention relates to a bone staple extraction device of the type comprising a first and a second element coupled together.

A bone staple is an implant that enables ligaments or soft tissue in general to be fixed to a bone structure.

The implant (ligament staple) is composed of a first element consisting of a titanium plate, preferably circular, from which four tips protrude into the bone, fixing the ligament, and a second element consisting of a polyether ether ketone (PEEK) thickness that enables the soft tissues to be better fixed to the bone, distributing the axial load over the entire contact surface. The first element overlaps, in contact, the second element, contained within the volume defined by the protruding tips.

Through the osseointegration process, the implant bonds to the bone tissue making it difficult to remove it in case of revision surgery.

Currently, the tools available on the market that enable the bone staples or the implant to be removed, in case of revision surgery, act as a lever by conveying the resistant forces directly onto the bone, increasing the risk factor for bone breakage.

The removal tools for such implants currently known, in fact, consist of a curved stainless steel bar, with a sharp side equipped with a double forked tip.

Along the stainless steel handle, there is a curved protruding element that acts as a fulcrum.

This instrument is wedged between the implant and the bone and, by acting as a lever on the fulcrum, enables the implant to be lifted and extracted.

This instrument concentrates the whole extraction force exerted by the surgeon in a single point, leading to the risk of bone breakage and other traumatic events for the patient. Moreover, as a result of osseointegration, the implant is difficult to remove and, therefore, it takes quite a long time to remove the bone staple from the patient's body.

Another example of a known type of bone staple extraction device is shown in the US document 2009/0264900.

The purpose of this invention is to overcome the drawbacks found in bone staple removal devices currently known and present in the prior art. Therefore, the purpose of this invention is to create a bone staple extraction device that enables an improved, easy, and rapid extraction of bone staples.

In addition, the purpose of this invention is to create a bone staple extraction device that enables an even distribution of the loads applied during the removal of the staple over the entire staple in order to avoid accidental breakage or excessive loads' being applied to only part of the patient's bone.

Finally, the purpose of this invention is to propose an extraction device for bone staples that is easy and quick for a surgeon to use.

These and other purposes are achieved with a bone staple extraction device as described in Claim 1.

SUMMARY

In particular, according to a first aspect, this invention concerns an extraction system comprising an extraction device and a bone staple.

The bone staple extraction device of the type provided with a first and a second overlapping element. Typically, the bone staple, with which the device to which this invention relates interacts, comprises a first element defined by a plate from which four tips, which penetrate the bone fixing the ligament, radiate out. The staple also comprises a second element formed by a body that can be placed, in contact, below the plate of the first element and enclosed within the volume defined by the four protruding tips. Both the first element and the second element have a central hole. The extraction device comprises a main gripping body that has a proximal and a distal end and a central rod sliding axially within the main gripping body, between a first and a second position.

The central rod comprises a proximal end and a distal end, the latter designed to be bound to the first element of the staple, particularly inside the hole of the first element of the staple. The axial sliding of the central rod promotes the disengagement of the bone staple from its seat: this occurs as a result of the engagement between the central rod and the first element of the staple and the subsequent ripping caused by the rapid upward translation of the staple. The extraction device also comprises movement means for moving the central rod and a multitude of abutment elements protruding from the distal end of the main gripping body and arranged circumferentially around the central rod. These abutment elements act on the second element of the bone staple to determine, in cooperation with the axial movement of the central rod, the separation of the second element of the staple from the first element of the staple and, consequently, the removal thereof. The second element of the staple is, in fact, kept in its position, therefore in contact with the patient's bone, as a result of the pressure exerted by the abutment elements and the surgeon pressing the extractor towards the patient's bone. The central rod, on the other hand, hooks the first element and tears it away during its upward translation, while the second element is held still by the abutment elements. In this way, the first element of the staple is torn away from the bone, while the second remains in contact only with the bone but without any connection to it: the two elements of the bone staple separate and the whole staple can be removed from its seat.

The movement means of the central rod comprise a first actuator, preferably a lever, and a mechanism that connects the first actuator to the central rod: this mechanism is designed to transform a rotary motion of the first actuator into a translatory movement of the central rod.

This mechanism is equipped with a rack, formed on the central rod, and a pinion, made at one end of the first actuator, so that the movement of the first actuator makes the pinion rotate, which, by engaging with the rack, promotes the axial translation of the central rod.

The movement means also comprise a second actuator positioned at the distal end of the central rod to promote an additional translation of the latter. This second actuator comes into operation when the first actuator is switched off.

The central rod slides between a first position, at which the distal end is contained within a volume defined by the multitude of abutment elements, and a second position, at which the distal end is completely extracted both from the main body and from the volume defined by the multitude of abutment elements. The central rod can also take on a third intermediate position between the first and second position.

In the first position of the central rod, the first actuator is in a lowered position, approaching the multitude of abutment elements, while in the intermediate position of the central rod, the first actuator is in a raised position, moving away from the multitude of abutment elements.

The device is also characterised in that, when the first actuator is in the raised position, the mechanism designed to transform a rotary movement of the first actuator into a translational motion of the central rod is deactivated and, therefore, pinion and rack are disengaged from each other.

The second actuator comprises a thrust surface, positioned at the proximal end of the central rod, acting on which the central rod moves from the intermediate position to the second position, when the first actuator is in the raised position and is therefore inactive.

The device also comprises an elastic spring-back element, inside the main gripping body and active between the central rod and the distal end of the main gripping body, to promote the return of the rod from the second position to the third intermediate position.

The distal end of the central rod has an edge at least partially protruding from the side wall of the rod, at a connection portion connecting to the side wall; the edge is designed to connect to an undercut made centrally along the inner edge of the central hole of the first element of the bone staple. This undercut is made between the first and second element of the bone staple, particularly below the first element.

At the third intermediate position, the connection portion connecting the side wall of the central rod and the edge of the distal end of the central rod is essentially contained in a plane containing the free thrust distal ends of the abutment elements or, alternatively, contained within the volume defined by the abutment elements, while the distal end of the central rod is outside the volume defined by the abutment elements.

The lever that defines the first actuator also comprises a striking surface on which an impulsive force is impressed to lower the lever, i.e. the first actuator, causing the central rod to suddenly translate from the third intermediate position to the first position, thus causing the first element of the staple to be torn from the second element, when the distal end of the central rod is engaged, due to interference with the undercut of the bone staple.

BRIEF DESCRIPTION OF THE DRAWINGS

This invention will be made clearer by the following detailed description, with reference to the attached drawings provided by way of example only, wherein.

DETAILED DESCRIPTION

The present description relates to a bone staple extraction system, comprising a bone staple extraction device 1 and a bone staple G.

In the above figures, the number 1 indicates in its entirety a bone staple extraction device in accordance with this invention.

In particular, the bone staples G (FIG. 6) that this device is able to remove are composed of two elements: a first element G1 consisting of a titanium plate, preferably circular, from which four tips P protrude that penetrate the bone fixing the ligament and a second element G2 consisting of a tablet-shaped body, then a polyether-ether-ketone (PEEK) thickness, placed, in contact, below the plate of the first element and enclosed within the volume defined by the four protruding tips P. The PEEK thickness enables the soft tissues to be better fixed to the bone, distributing the axial load over the entire contact surface. At the centre of each element G1 and G2, in the axial position, the bone staple G has a through hole F to enable the coupling with the extraction device 1 as described below.

Figure 6:
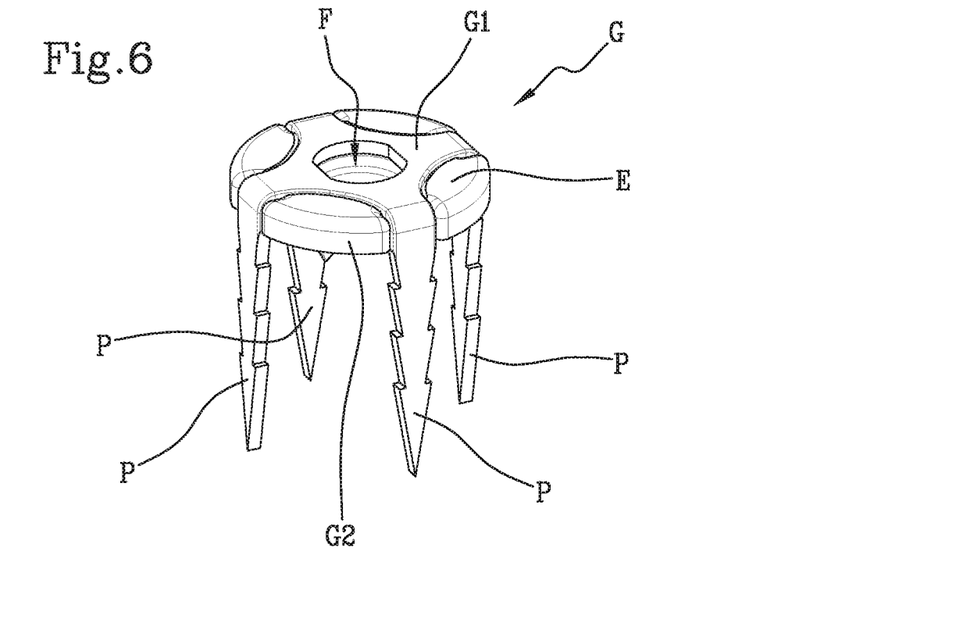
FIG. 6 illustrates a perspective view of a removable bone staple with the device to which this invention relates.

The central holes of the first and second element coincide.

In the following, explicit reference will be made to the terms "proximal" meaning a portion of the device that is closer to the user's body, thus to the surgeon who holds it; "distal" refers to a portion of the device that is further from the user's body, thus further from the surgeon.

The device 1 comprises a main gripping body 2, which has a distal end 2d and a proximal end 2p, and a central rod 3 that slides inside the central gripping body 2 along an axis 2a.

The central rod 3 also comprises a corresponding proximal end 3p and a distal end 3d, the latter being designed to bind with the first element of the staple G1, in particular with the central hole made in the bone staple.

The extraction device 1 comprises, in addition, movement means 4 of the central rod 3 that enable the central rod 3 to axially slide, inside the main gripping body 2, between a first position and a second position, as will be described below.

The main gripping body 2 has, protruding from the distal end 2d, a multitude of abutment elements 5, arranged circumferentially around the central rod 3. These abutment elements 5 protrude axially from the distal end 2d of the main body 2 and have free distal ends 5d that act on the second element of the staple to determine, in cooperation with the movement of the central rod 2, the separation of the second element of the staple from the first element of the staple and the removal thereof. The free distal ends 5d of the abutment elements 5 are preferably coplanar and belong to the same plane X.

In detail, the central hole F of the bone staple G is defined by a first central hole F1, made in the first element G1, and by a second central hole F2, made in the second element G2 of the bone staple G; the first central hole F1 and the second central hole F2 are overlapped and create, when the two elements G1 and G2 are coupled, an undercut S placed below the perimeter edge of the hole F of the first element G1 of the bone staple G. The distal end 3d of the central rod 3 has an edge 6 at least partially protruding from the side wall 3L of the rod 3 near a connection portion 7 with the side wall 3L of the central rod 3 (FIG. 6).

The edge 6 is designed to connect, by interference, with the above-mentioned undercut S made centrally in the first element G1 of the bone staple G.

Advantageously, the edge 6 of the distal end 3d of the central rod 3 can be shaped elliptically or have at least two parts that protrude further than the rest of the perimeter of this edge 6.

The hole of the first element G1 is counter-shaped to the perimeter profile of the edge 6 protruding from the distal end 3d of the central rod 3, to enable the insertion of the distal end 3d of the central rod 3.

Figure 7A:
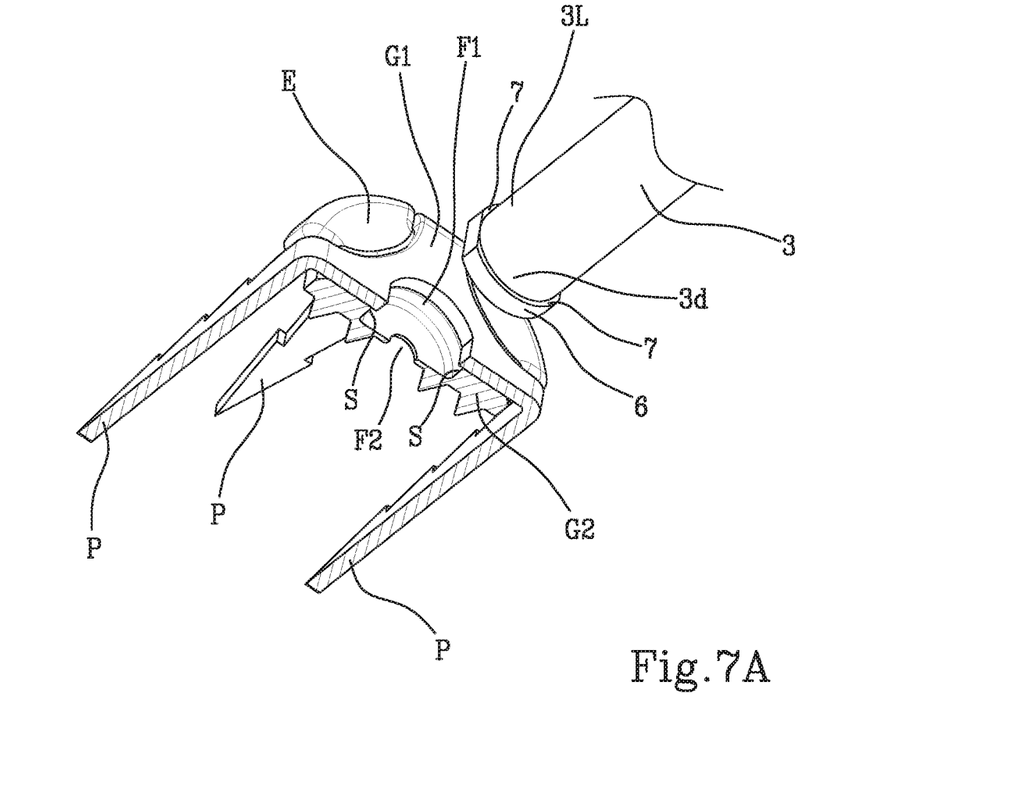
FIGS. 7A-7C illustrate, in enlarged form, a hooking sequence between the device to which this invention relates and a bone staple illustrated in FIG. 6.
Figures 7B, 7C:
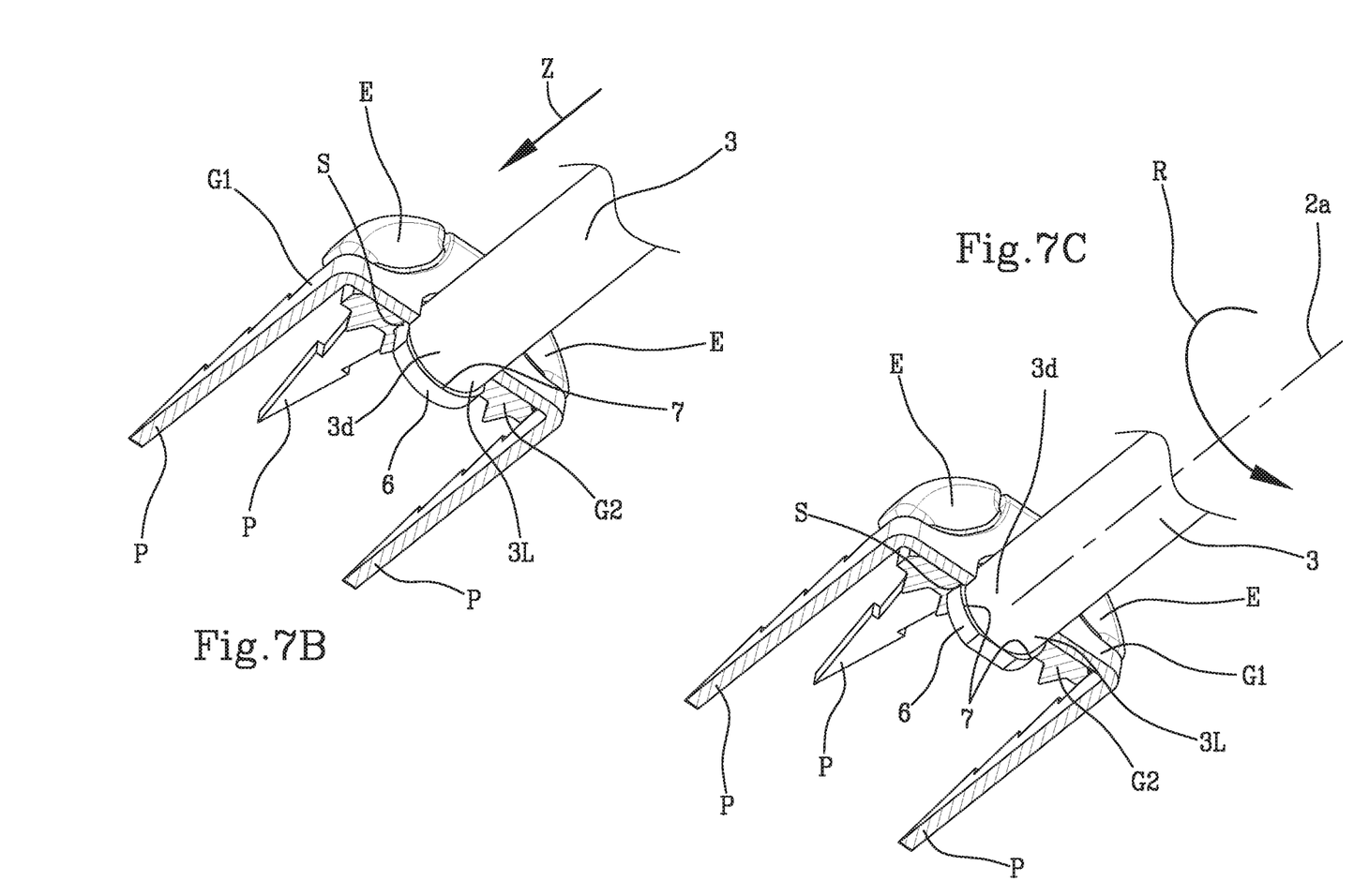

The distal end 3d of the central rod 3 is inserted inside the central hole F of the bone staple G along an axial direction Z (FIG. 7B) coinciding with the axis 2a of the central body 2, and the whole device 1 is rotated around this axis 2a (see the arrow R in FIG. 7C) until the edge 6 of the distal end 3d of the central rod 3 is engaged with the undercut S, thus hooking the central rod 3 to the bone staple G.

The first element G1 of the bone staple G is shaped so as to leave portions E of the second element G2, placed below, exposed.

The abutment elements 5 abut against these portions E, in particular the free distal ends 5d, which keep the second element G2 still in position while the central rod 3, engaged with the first element G1 of the bone staple G, slides axially upwards, dragging and separating the first element G1 from the second element G2, thus enabling the removal of the bone staple G from the patient's body.

The axial sliding of the rod, which entails the removal, by tearing, of the staple, is quick, instantaneous, and generated by an active impulse force on the movement means 4.

The axial sliding of the central rod 3, both in one direction and in the other, occurs, thus, by means of the above-mentioned movement means 4, now described in detail.

These movement means 4 of the central rod 3 comprise a first actuator 8, preferably a lever, and a mechanism 9 that connects the first actuator 8 to the central rod 3: this mechanism 9 is designed to transform the rotary motion of the first actuator 8, thus of the lever, into a translational motion of the central rod 3.

Specifically, this mechanism 9 comprises a rack 10 formed directly on the central rod 3 and a pinion 11, made at one end of the lever that defines the first actuator 8, so that the movement of the first actuator, and, thus, of the lever, rotates the pinion 11 that, engaging with the rack 10, causes the axial translation of the central rod 3.

Figure 9:
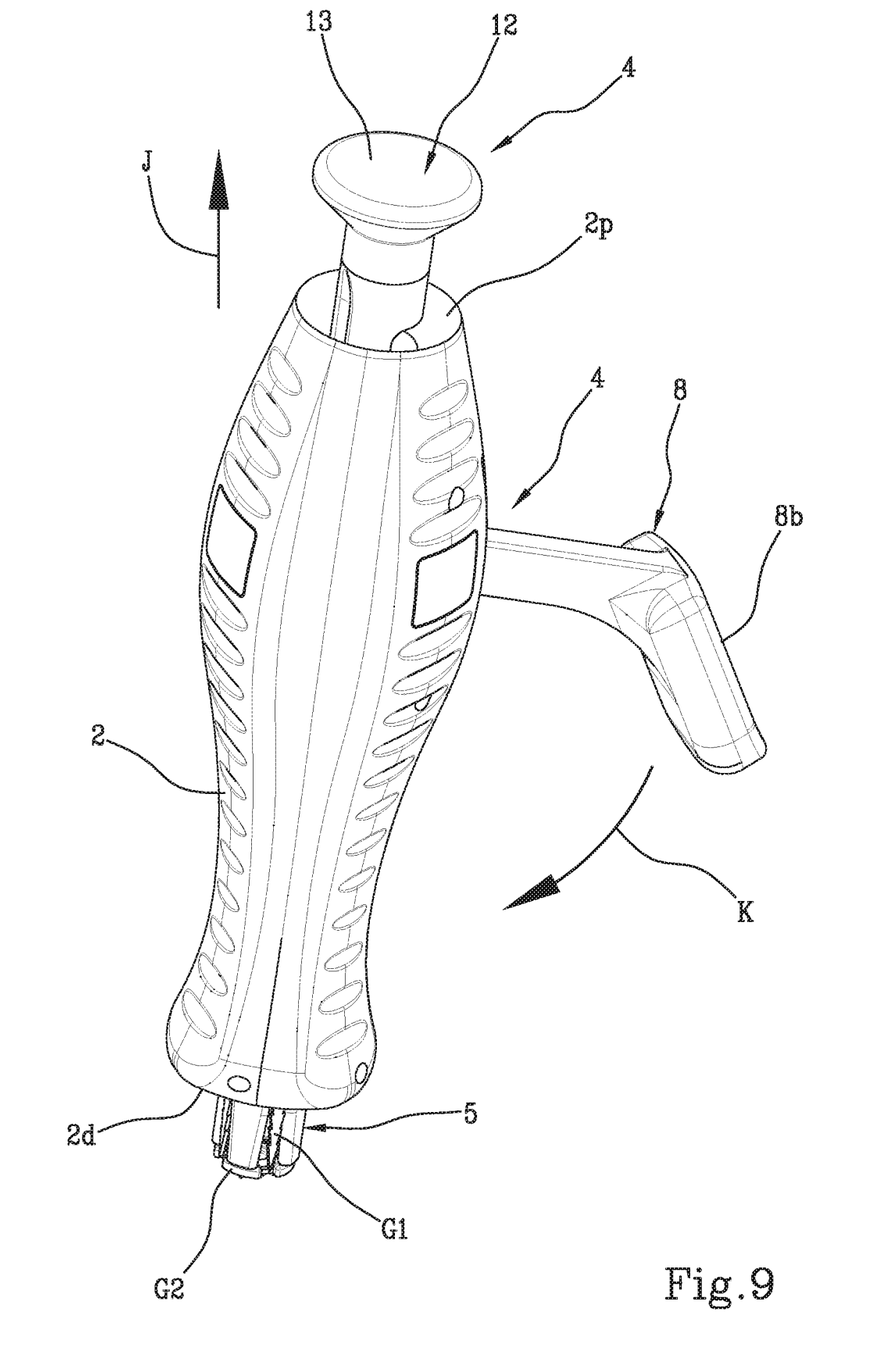
FIG. 9 illustrates a view of the removal device associated with a bone staple after the removal thereof.

The central rod 3 can slide between a first position (illustrated in FIG. 3), in which the distal end 3d of the central rod 3 is contained inside a volume V defined by the plurality of abutment elements 5, and a second position (illustrated in FIG. 4), in which the distal end 3d is completely extracted both from the main body 2 and from the volume V defined by the plurality of abutment elements 5. The rod 3 can also assume a third intermediate position (illustrated in FIG. 5) between the first and the second position. The first actuator, or lever, 8 has a striking surface 8b, on which a percussion is exerted that makes it move, in particular, it lowers it (FIGS. 3 and 9); as illustrated in FIG. 9: the impulse forced impressed on the striking surface 8b of the first actuator 8 (see arrow K) is enough to raise the central rod 3 (arrow J) with a sudden snap and tear the first element G1 from the bone, when the central rod 3 is engaged with it.

Figure 1:
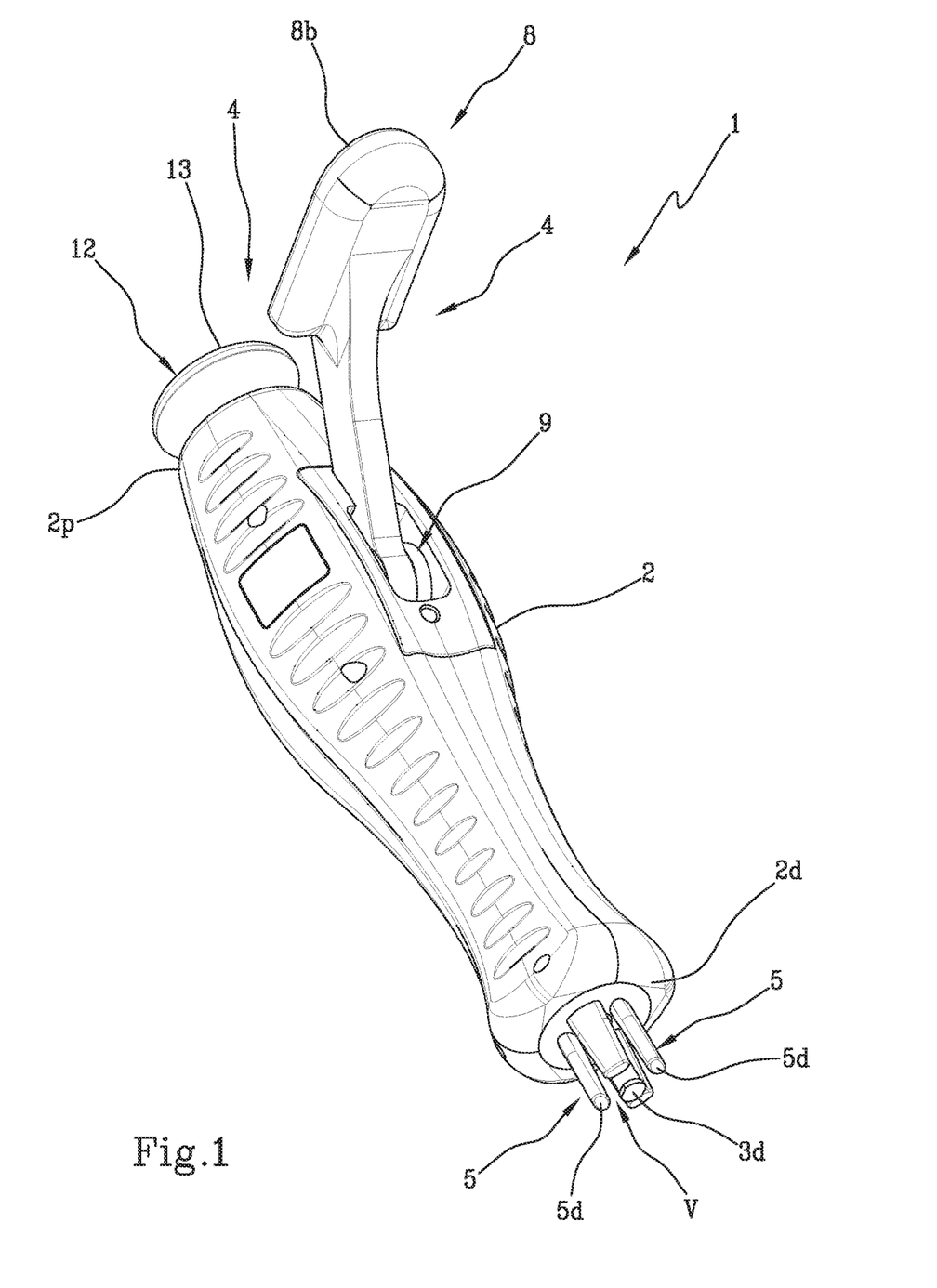
FIG. 1 illustrates a perspective view of a bone staple extraction device according to this invention.
Figure 2:
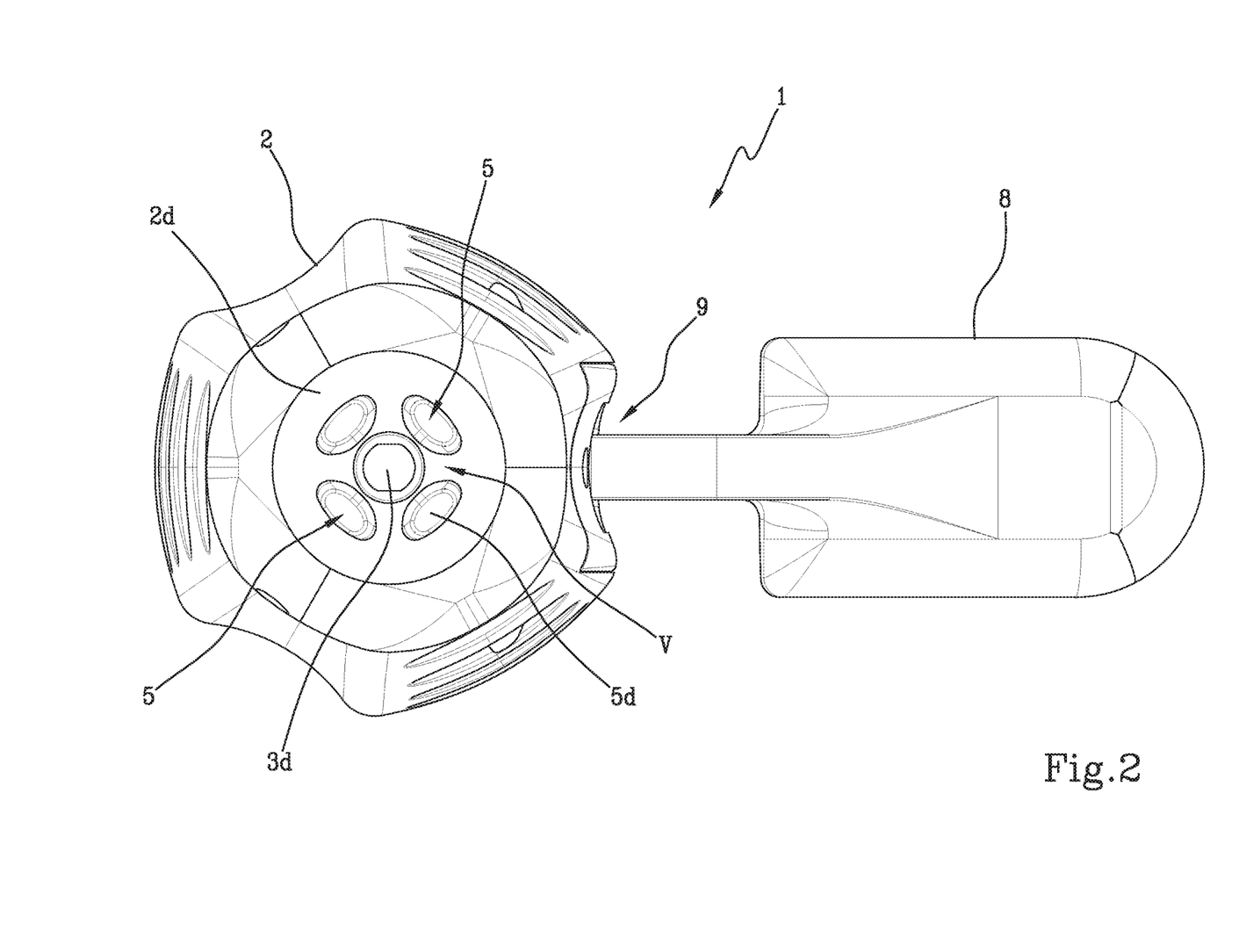
FIG. 2 illustrates a front view of the device illustrated in FIG. 1.
Figure 3:
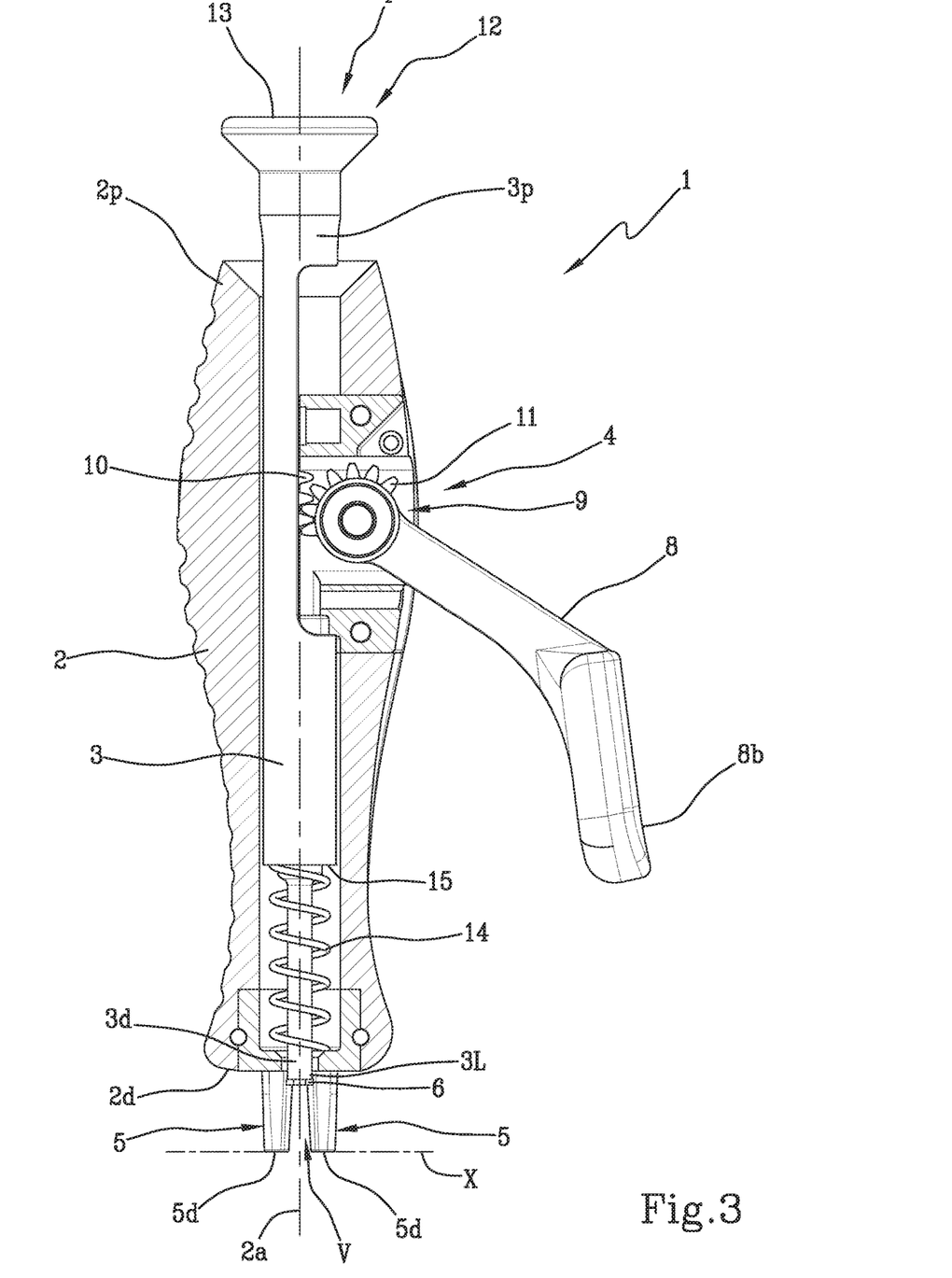
FIG. 3 shows a cross-section view of the device to which this invention relates, in a first operating position.
Figure 5:
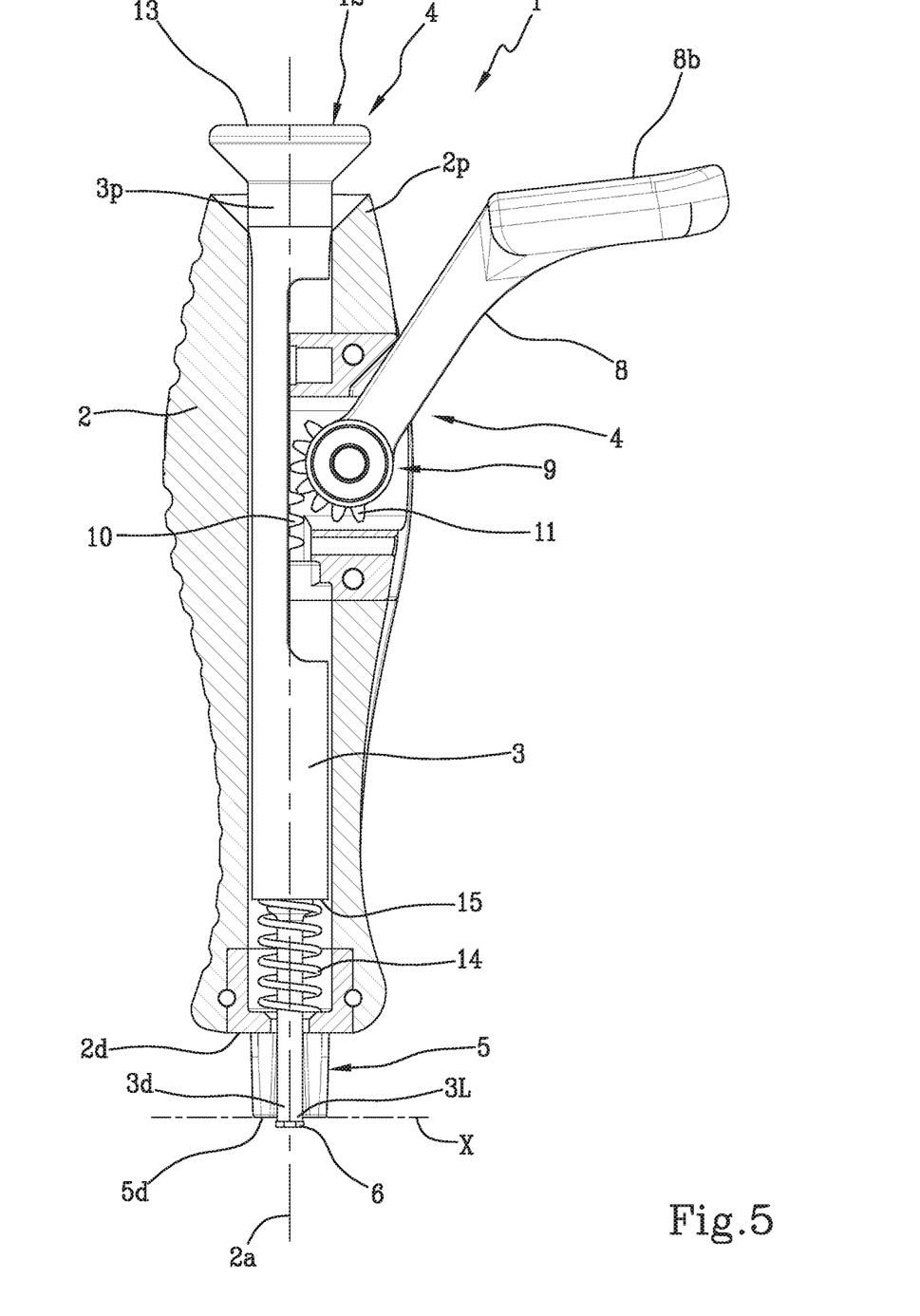
FIG. 5 shows a cross-section view of the device to which this invention relates in a third operating position.

As can be seen in FIG. 3, in the first position, the first actuator 8 is in a lowered position, approaching the plurality of abutment elements 5, while in the third intermediate position, as can be seen in FIG. 5, the first actuator 8 is in a raised position, moving away from the multitude of abutment elements 5.

Figure 8:
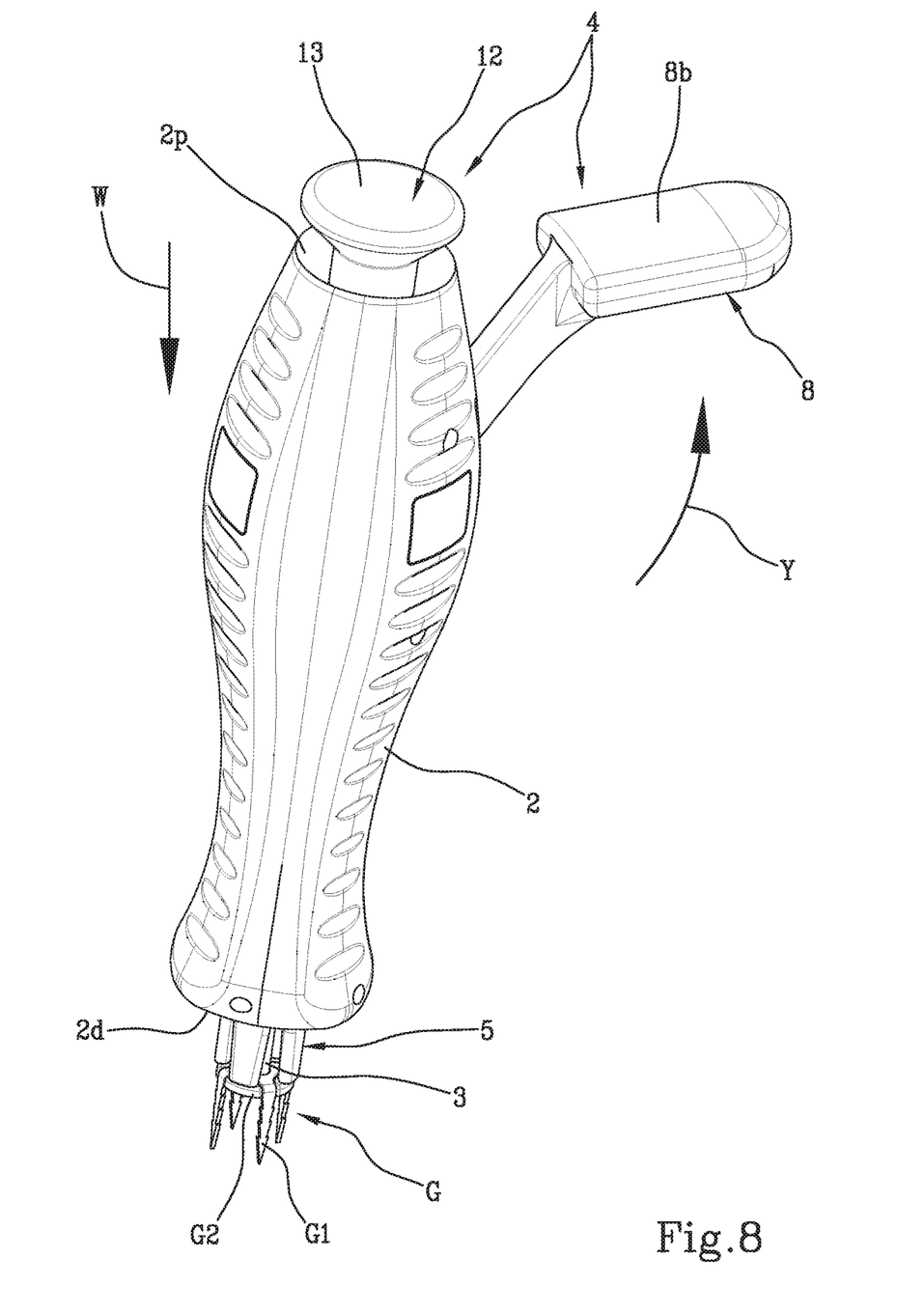
FIG. 8 shows a prospective view of the removal device associated with a bone staple, prior to the removal thereof, then in an intermediate operating step.

Lifting the first actuator 8 (FIG. 8 arrow Y) causes the central rod 3 to be partially lowered from the first position to the intermediate position (FIG. 8 arrow W). When the first actuator 8 is completely raised, the central rod 3 can be in the second or in the third intermediate position.

Figure 4:
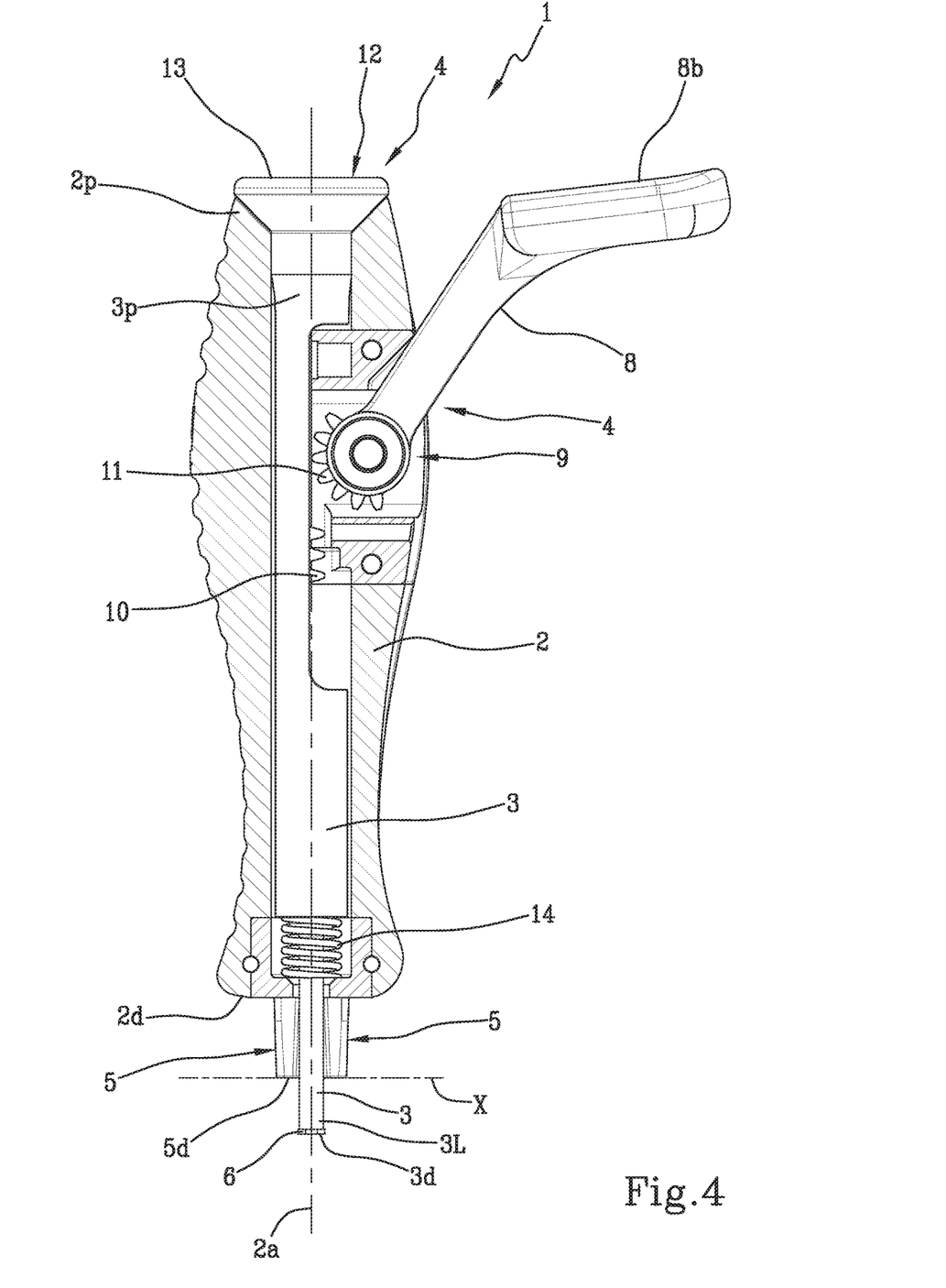
FIG. 4 shows a cross-section view of the device to which this invention relates, in a second operating position.

In fact, when the first actuator 8 is completely raised (FIGS. 4, 5, and 8, arrow Y), the central rod 3 is in third intermediate position (FIG. 5) and the mechanism 9 designed to transform a rotary motion of the first actuator into a translational motion of the central rod is deactivated; this means that the pinion 11 and rack 10 are disengaged from each other, thus enabling the central rod 3 to freely slide and bring itself into the second position (FIG. 4). In particular, the axial sliding of the rod is enabled by means of a second actuator 12 (FIG. 4).

When the first actuator, or lever, 8 is completely lowered (FIG. 3), in contrast, and, thus, the central rod 3 is in the first position, the activation of the second actuator 12 is uninhibited since the pinion 11 and rack 10 are engaged with each other. The rod, therefore, cannot freely slide being blocked by the engagement of the pinion 11 with the rack 10.

The movement means 4 also comprise, therefore, a second actuator 12 positioned at the proximal end 3p of the central rod 3 to promote an additional translation of the central rod 3.

The second actuator 12 comprises a thrust surface 13, positioned at the proximal end 3p of the central rod 3 acting on which, with a downwards axial thrust force, the central rod 3 passes from the intermediate position to the second position. This is possible when the lever 8 is in the raised position and the pinion and rack are disengaged.

The device 1 comprises, in addition, an elastic spring-back element 14, preferably a helical spring, inside the main gripping body 2 and active between the central rod 3 and the distal end 2d of the main gripping body 2, in particular between one shoulder 15 of the central rod 3 and the inside of the distal end 2d of the central rod 2. This elastic element 14 enables the central rod 2 to return upwards, following the release of the force exerted on the thrust surface 13 of the proximal end 3p of the central rod 3.

The second position (FIG. 4), thus that in which the distal end 3d of the central rod 3 is completely extracted from the volume V defined by the abutment elements 5, is that where the bone staple G is hooked, the distal end 3d being completely free and exposed. Even in this position, the lever 8 is raised and approaching the proximal end 2p of the main body 2.

The third intermediate position (FIG. 5), in contrast, corresponds to the position in which the lever 8 is raised and the connecting portion 7 between the side wall 3L of the central rod 3 and the edge 6 of the distal end 3d of the central rod 3 basically overlaps or coincides with a plane X containing free thrust distal ends 5d of the abutment elements 5 or is contained inside the volume V by the abutment elements 5, while the distal end 3d of the central rod 3 is external to this volume V.

In use, when a bone staple G, of the type described above, needs to be removed from the body of a patient, the lever 8 is completely raised to bring the central rod 3 into the third intermediate position (FIG. 5) and to thus disengage pinion 11 and rack 10.

Acting on the second actuator 12, by thus exerting a downwards thrust on the thrust surface 13, positioned at the proximal end 3p of the central rod 2, the distal end 3d is made to exit the central rod 3 from the volume V defined by the abutment elements 5. In this configuration, it is possible to hook the device 1 to the staple G by inserting the distal end 3d into the hole F of the bone staple G. The device is rotated until the edge 6 is connected and engaged, by interference, to the above-mentioned undercut S, centrally made between the first element G1 and the second element G2 of the bone staple G.

At this point, the thrust is released on the second actuator 12, so that the elastic spring-back element 14 raises the central rod 3, thus bringing the abutment elements 5 into contact with the exposed portions E of the second element G2 of the staple G. The central rod 3 is thus positioned in the third intermediate position, in which the distal end 3d of the central rod 3, engaged with the staple G, is basically at the free distal ends 5d of the abutment elements 5 that, as mentioned beforehand, are thus brought into contact with the staple, in particular with the respective exposed portions E of the staple G.

Up to this point (second and third position), the lever 8 is in the raised position: at this point, a force is exerted on the striking surface 8b so as to impress an impulse on the lever 8 that lowers the lever itself and axially raises the central rod 3 upwards to tear the first element G1 from the bone.

The central rod 3 is, thus, brought into the first position (FIG. 3), at which the distal end 3d of the central rod 3 is completely contained in the volume V defined by the abutment elements 5. The central rod 3 exerts a traction force on the first element G1 of the staple G and drags it along upwards, while the second element G2 is kept in position in contact with the patient's body following the pressure exerted on the exposed portions E by the abutment elements 5.

Once the first element G1 has been torn off, the second element G2 can be removed with other tools.

The invention achieves its intended purpose as it allows a quick and complete extraction of the bone staple by distributing the force evenly over the whole staple. This prevents accidental breakage of the staple itself or damage to the patient that can occur if the extraction force is concentrated on a single point.

The mechanical stresses are absorbed by the second element of the bone staple made of PEEK. No momentum is exerted on the staple, but an axial pull with a sharp blow that causes the immediate detachment of the first element from the second element. The impulsive force impressed on the first actuator is necessary since the staple undergoes osteointegration.

The device is also easy and handy for the surgeon to use and safe for the patient.

The invention claimed is:

1. An extraction system comprising an extraction device and a bone staple, wherein the bone staple is provided with a first element comprising a plate, having a central through hole, from which four tips extend and a second element, having a central through hole, configured to be placed, in contact, below the plate of the first element and enclosed inside a volume defined by the four tips, said extraction device comprising a main gripping body which has a proximal end and a distal end, a central rod comprising a proximal end and a distal end, said distal end of said central rod being adapted to directly couple with the first element of said staple; said central rod being axially slidable within the main gripping body between a first position and a second position; wherein the extraction device further comprises movement means for moving the central rod and a plurality of abutment elements protruding axially from said distal end of the main gripping body and arranged circumferentially around the central rod, adapted to act on the second element of the staple to obtain, in cooperation with the movement of the central rod, separation of the second element of the staple from the first element of the staple and removal of the first element.

2. The system according to claim 1, wherein said movement means of the central rod comprise a first lever actuator and a mechanism that connects said first lever actuator to said central rod, said mechanism being adapted to transform a rotary motion of the first lever actuator into a translational motion of the central rod.

3. The system according to claim 2, wherein said mechanism is provided with a rack formed on said central rod and a pinion, associated with said first lever actuator, so that the movement of said first lever actuator rotates the pinion that, engaging said rack, promotes axial translation of the central rod.

4. The system according to claim 3, wherein said first lever actuator has a striking surface on which a percussion is applied that moves said first lever actuator, lowering it.

5. The system according to claim 2, wherein said movement means comprise a second actuator, positioned at said proximal end of the central rod, to promote a further translation of the central rod.

6. The system according to claim 5, wherein the central rod slides between the first position, at which the distal end of the central rod is contained within a volume defined by the plurality of abutment elements, the second position, at which said distal end is completely extracted both from the main body and from the volume defined by the plurality of abutment elements; and wherein said central rod is able to be positioned in a third intermediate position between the first and second positions.

7. The system according to claim 6, wherein at said first position of the central rod, said first lever actuator is in a lowered position, approaching the plurality of abutment elements, and at said third intermediate position of the central rod said first lever actuator is in a raised position, moving away from the plurality of abutment elements.

8. The system according to claim 7, wherein when said first lever actuator is in the raised position, away from the plurality of abutment elements, the mechanism designed to transform the rotary motion of the first lever actuator into a translational motion of the central rod, is deactivated.

9. The system according to claim 7, wherein said second actuator comprises a thrust surface, positioned at said proximal end of the central rod, acting on which the central rod passes from the third intermediate position to the second position, when said first lever actuator is in the raised position.

10. The system according to claim 9, further comprising an elastic spring-back element placed inside the main gripping body and active between the central rod and an internal portion of the distal end of the main gripping body.

11. The system according to claim 6, wherein the distal end of the central rod has an edge at least partially protruding from a side wall of the central rod, at a connection portion for connecting to the side wall; said edge being adapted to connect to an undercut formed centrally between the first and the second element of the staple, below the first element of said bone staple.

12. The system according to claim 11, wherein at said third intermediate position, the connection portion between the side wall of the central rod and the edge of said distal end of the central rod substantially overlaps with a plane containing free distal thrust ends of said abutment elements or contained within the volume defined by said abutment elements, while the distal end of the central rod is external to said volume.

* * * * *